US011376120B2

(12) United States Patent
Costello

(10) Patent No.: US 11,376,120 B2
(45) Date of Patent: Jul. 5, 2022

(54) MITRAL VALVE PROSTHESIS FOR TRANSCATHETER VALVE IMPLANTATION

(71) Applicant: MEDTRONIC VASCULAR GALWAY, Ballybrit (IE)

(72) Inventor: Declan Costello, Ballybrit (IE)

(73) Assignee: MEDTRONIC VASCULAR GALWAY, Ballybrit (IE)

( * ) Notice: Subject to any disclaimer, the term of this patent is extended or adjusted under 35 U.S.C. 154(b) by 73 days.

(21) Appl. No.: 17/073,534

(22) Filed: Oct. 19, 2020

(65) Prior Publication Data

US 2021/0045867 A1 Feb. 18, 2021

Related U.S. Application Data

(60) Continuation of application No. 15/873,595, filed on Jan. 17, 2018, now Pat. No. 10,813,750, which is a division of application No. 13/955,177, filed on Jul. 31, 2013, now Pat. No. 9,895,219.

(51) Int. Cl.
*A61F 2/24* (2006.01)

(52) U.S. Cl.
CPC .......... *A61F 2/2412* (2013.01); *A61F 2/2418* (2013.01); *A61F 2/2436* (2013.01);
(Continued)

(58) Field of Classification Search
CPC .... A61F 2/02; A61F 2/022; A61F 2/04; A61F 2/06; A61F 2/062; A61F 2/064;
(Continued)

(56) References Cited

U.S. PATENT DOCUMENTS

| 4,079,468 A | 3/1978 | Liotta et al. |
| 6,010,531 A | 1/2000 | Donlin et al. |

(Continued)

FOREIGN PATENT DOCUMENTS

| DE | 4316971 A1 | 11/1994 |
| WO | 2008063537 A2 | 5/2008 |

(Continued)

OTHER PUBLICATIONS

PCT/US2014/045300, PCT International Search Report, dated Dec. 18, 2014.

(Continued)

*Primary Examiner* — Wade Miles
*Assistant Examiner* — Kankindi Rwego
(74) *Attorney, Agent, or Firm* — Medler Ferro Woodhouse & Mills PLLC

(57) ABSTRACT

A transcatheter valve prosthesis is disclosed that has a compressed, delivery configuration and an expanded configuration for deployment within a native heart valve. The valve prosthesis includes a self-expanding frame and a prosthetic valve component. The self-expanding frame includes a valve receiving portion defining an opening therethrough and first and second anchors at opposing ends of the valve receiving portion. The valve receiving portion is substantially planar and the first and second anchors are oriented substantially perpendicular to the valve receiving portion when the valve prosthesis is in the expanded configuration. The prosthetic valve component is disposed within the opening of the valve receiving portion and secured thereto.

20 Claims, 7 Drawing Sheets

(52) U.S. Cl.
CPC ..... *A61F 2/2409* (2013.01); *A61F 2220/0016* (2013.01); *A61F 2230/0008* (2013.01)

(58) Field of Classification Search
CPC .... A61F 2/07; A61F 2/82; A61F 2/844; A61F 2/848; A61F 2/92; A61F 2/95; A61F 2/962; A61F 2/966; A61F 2/2409; A61F 2/2412; A61F 2/2415; A61F 2002/02; A61F 2002/041; A61F 2002/043; A61F 2002/044; A61F 2002/045; A61F 2002/046; A61F 2002/047; A61F 2002/048; A61F 2002/061; A61F 2002/065; A61F 2002/067; A61F 2002/068; A61F 2002/072; A61F 2002/075; A61F 2002/077; A61F 2002/8483; A61F 2002/8486; A61F 2220/0016; A61F 2230/0008
USPC ...................................................... 623/2.11
See application file for complete search history.

(56) References Cited

U.S. PATENT DOCUMENTS

| | | | |
|---|---|---|---|
| 6,190,311 B1 | 2/2001 | Glines et al. | |
| 6,451,054 B1 | 9/2002 | Stevens | |
| 6,564,805 B2 | 5/2003 | Garrison et al. | |
| 6,974,476 B2 * | 12/2005 | McGuckin, Jr | A61F 2/2436 623/2.11 |
| 7,374,571 B2 | 5/2008 | Pease et al. | |
| 8,366,766 B2 | 2/2013 | Berreklouw | |
| 9,572,661 B2 | 2/2017 | Robin et al. | |
| 10,517,725 B2 | 12/2019 | Gifford, III et al. | |
| 10,813,750 B2 * | 10/2020 | Costello | A61F 2/2436 |
| 2006/0195183 A1 | 8/2006 | Navia et al. | |
| 2007/0005129 A1 | 1/2007 | Damm et al. | |
| 2007/0073387 A1 | 3/2007 | Forster et al. | |
| 2010/0185275 A1 * | 7/2010 | Richter | A61F 2/2439 623/2.11 |
| 2012/0203336 A1 | 8/2012 | Annest | |
| 2013/0035759 A1 | 2/2013 | Gross et al. | |

FOREIGN PATENT DOCUMENTS

| | | |
|---|---|---|
| WO | 2013021374 A2 | 2/2013 |
| WO | 2013028387 A2 | 2/2013 |
| WO | 2013076724 A2 | 5/2013 |

OTHER PUBLICATIONS

Suzuki et al., "Left Thoracotomy for Multiple-Time Redo Mitral Valve Surgery Using On-Pump Beating Heart Technique" Ann Thorac Surg 2008; 86:466-471.
Annular Definition, American Heritage Dictionary.

\* cited by examiner

MITRAL VALVE PROSTHESIS FOR TRANSCATHETER VALVE IMPLANTATION

CROSS-REFERENCE TO RELATED APPLICATIONS

This application is a continuation of prior U.S. application Ser. No. 15/873,595, filed on Jan. 17, 2018, which is a divisional of prior U.S. application Ser. No. 13/955,177, filed on Jul. 31, 2013, now U.S. Pat. No. 9,895,219, each of which is hereby incorporated by reference in its entirety for all purposes.

FIELD OF THE INVENTION

The invention relates to a prosthetic valve for percutaneously replacing a native valve or a previously implanted prosthetic valve in a transcatheter or minimally invasive procedure.

BACKGROUND OF THE INVENTION

A wide range of medical treatments are known that utilize "endoluminal prostheses." As used herein, endoluminal prostheses are intended to include medical devices that are adapted for temporary or permanent implantation within a body lumen, including both naturally occurring and artificially made lumens. Examples of lumens in which endoluminal prostheses may be implanted include but are not limited to arteries, veins, gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets disposed within the interior of the stent structure. The prosthetic valve can be reduced in diameter, by being contained within a sheath component of a delivery catheter or by crimping onto a balloon catheter, and advanced through the venous or arterial vasculature. Once the prosthetic valve is positioned at the treatment site, for instance within an incompetent native or previously implanted prosthetic valve, the stent structure may be expanded to hold the prosthetic valve firmly in place. One embodiment of a prosthetic valve having a stent structure is disclosed in U.S. Pat. No. 5,957,949 to Leonhardt et al. entitled "Percutaneous Placement Valve Stent," which is incorporated by reference herein in its entirety.

A human heart includes two atrio-ventricular valves through which blood flows from the atria to the ventricles, the valves functioning to prevent return of blood to the atrium. The tricuspid valve, also known as the right atrio-ventricular valve, is a tri-flap valve located between the right atrium and the right ventricle. The mitral valve, also known as the bicuspid or left atrioventricular valve, is a dual-flap valve located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function. The mitral valve includes two moveable leaflets, an anterior leaflet and a posterior leaflet, that each open and close in response to differential pressures on either side of the valve. Ideally, the leaflets move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with mitral regurgitation or backflow typically having relatively severe physiological consequences to the patient.

Due to the different physical characteristics of the mitral valve as compared to other valves such as the pulmonary valve, percutaneous implantation of a valve in the mitral position has its own unique requirements for valve replacement. There is a continued desire to improve mitral valve replacement devices and procedures to accommodate the structure of the heart, including by providing improved devices and methods for replacing the mitral valve percutaneously.

BRIEF SUMMARY OF THE INVENTION

Embodiments hereof are directed to a transcatheter valve prosthesis having a compressed, delivery configuration and an expanded configuration for deployment within a native heart valve. The valve prosthesis includes a self-expanding frame and a prosthetic valve component. The self-expanding frame includes a valve receiving portion defining an opening therethrough and first and second anchors at opposing ends of the valve receiving portion. The valve receiving portion is substantially planar with a longitudinal length that is greater than a transverse width and the first and second anchors are oriented substantially perpendicular to the valve receiving portion when the valve prosthesis is in the expanded configuration. The prosthetic valve component is disposed within the opening of the valve receiving portion and secured thereto.

Embodiments hereof are also directed to transcatheter valve prosthesis having a compressed, delivery configuration and an expanded configuration for deployment within a native heart valve. The valve prosthesis includes a self-expanding frame, a prosthetic valve component, and a plurality of barbs. The self-expanding frame includes a valve receiving portion defining an opening therethrough, the valve receiving portion being substantially planar and having opposing upstream and downstream surfaces that extend between opposing first and second ends, and first and second anchors respectively disposed at the first and second ends of the valve receiving portion, each anchor being a thin plate with opposing first and second edges. The first and second anchors are oriented substantially perpendicular to the valve receiving portion when the valve prosthesis is in the expanded configuration such that the first edge of each anchor extends upstream of the upstream surface of the valve receiving portion and the second edge of each anchor extends downstream of the downstream surface of the valve receiving portion. The prosthetic valve component is disposed within the opening of the valve receiving portion of the frame and secured thereto. The barbs are coupled to each of the first and second anchors, such that the barbs extend outwardly away from the frame.

Embodiments hereof are also directed to a method of percutaneously delivering and deploying a valve prosthesis within a native mitral valve of a heart. A delivery system is introduced through a left-sided thoracotomy, the delivery system having the valve prosthesis mounted therein. The valve prosthesis includes a self-expanding frame, the frame having a valve receiving portion defining an opening therethrough and proximal and distal anchors at opposing ends of the valve receiving portion, and a prosthetic valve component disposed within the opening of the valve receiving portion of the frame. The delivery system is advanced to the heart and through a wall of the atrium until at least a portion of the valve prosthesis is disposed within the native mitral valve. An outer sheath of the delivery system is retracted to deploy the distal anchor of the valve prosthesis, wherein the distal anchor is oriented substantially perpendicular to the valve receiving portion of the frame when deployed. The distal anchor of the valve prosthesis is secured to a wall of the heart, wherein a native anterior leaflet of the native mitral valve is thereby pinned between the wall of the heart and the distal anchor. The outer sheath of the delivery system is further retracted to deploy the proximal anchor of the valve prosthesis, wherein the proximal anchor is oriented substantially perpendicular to the valve receiving portion of the frame when deployed. The proximal anchor of the valve prosthesis is secured to the wall of the heart, wherein a native posterior leaflet of the native mitral valve is thereby pinned between the wall of the heart and the proximal anchor.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

The following detailed description is merely exemplary in nature and is not intended to limit the invention or the application and uses of the invention. Although the description of embodiments hereof is in the context of mitral heart valve replacement, the invention may be adapted to be used for other valve replacement where it is deemed useful. Furthermore, there is no intention to be bound by any expressed or implied theory presented in the preceding technical field, background, brief summary or the following detailed description.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Further the term "self-expanding" is used in the following description with reference to the frame of the valve prosthesis and is intended to convey that the frame components are shaped or formed from a material that has a mechanical memory to return to an expanded deployed configuration from a compressed or constricted delivery configuration. Non-exhaustive exemplary materials that may be rendered self-expanding include stainless steel, a pseudo-elastic metal such as a nickel titanium alloy or nitinol, various polymers, and a so-called super alloy, which may have a base metal of nickel, cobalt, chromium, or other metal. Mechanical memory may be imparted to material used to form the frame by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Figure 1:
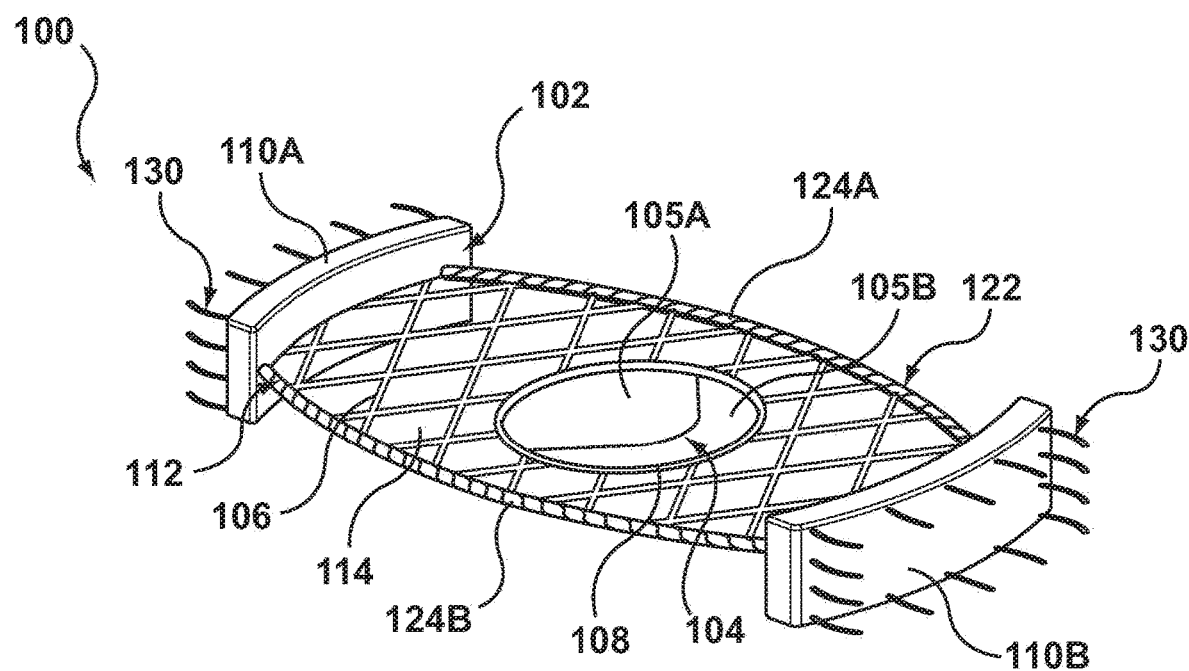
FIG. 1 is a perspective view of a valve prosthesis in an expanded configuration in accordance with an embodiment hereof.
Figure 4:
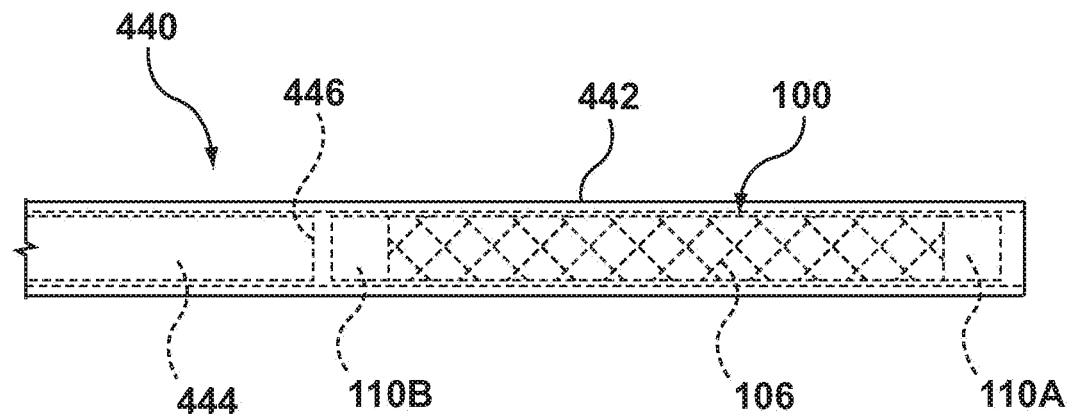
FIG. 4 is a side view of a distal portion of a delivery catheter with the valve prosthesis of FIG. 1 in a compressed delivery configuration therein.
Figure 5:
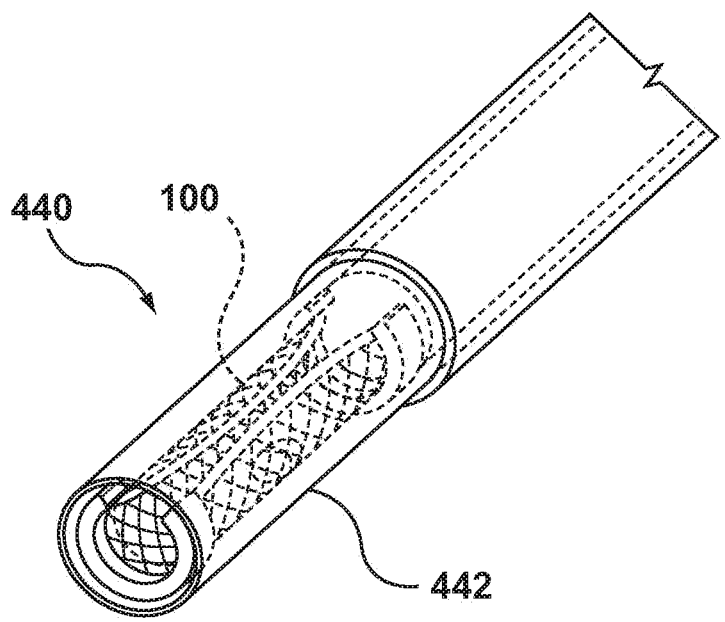
FIG. 5 is a distal end view of the distal portion of the delivery catheter of FIG. 4 with the valve prosthesis of FIG. 1 in a compressed delivery configuration therein.

Embodiments hereof are related to a valve prosthesis configured for deployment within the mitral valve of the heart in a transcatheter heart valve implantation procedure. FIG. 1 is a perspective view of a valve prosthesis 100 in an expanded, deployed configuration in accordance with an embodiment hereof, with FIGS. 2 and 3 being side and top views, respectively, of valve prosthesis 100 in the expanded, deployed configuration. FIG. 4 is a side view of a distal portion of a delivery catheter 440 with valve prosthesis 100 in a compressed, delivery configuration therein, and FIG. 5 is a distal end perspective view of valve prosthesis 100 in the compressed, delivery configuration within the delivery catheter.

Valve prosthesis 100 includes a self-expanding frame 102 and a prosthetic valve component 104. Self-expanding frame 102 includes a valve receiving portion 106 defining a central opening 108 therethrough and first and second anchors 110A, 110B at opposing ends of the valve receiving portion. Valve receiving portion 106 is substantially planar and the first and second anchors 110A, 110B are oriented substantially perpendicular to the valve receiving portion when valve prosthesis 100 is in the expanded, deployed configuration of FIGS. 1-3 as will be discussed in more detail herein. Prosthetic valve component 104 is disposed within central opening 108 of valve receiving portion 106 and secured thereto.

Figure 2:
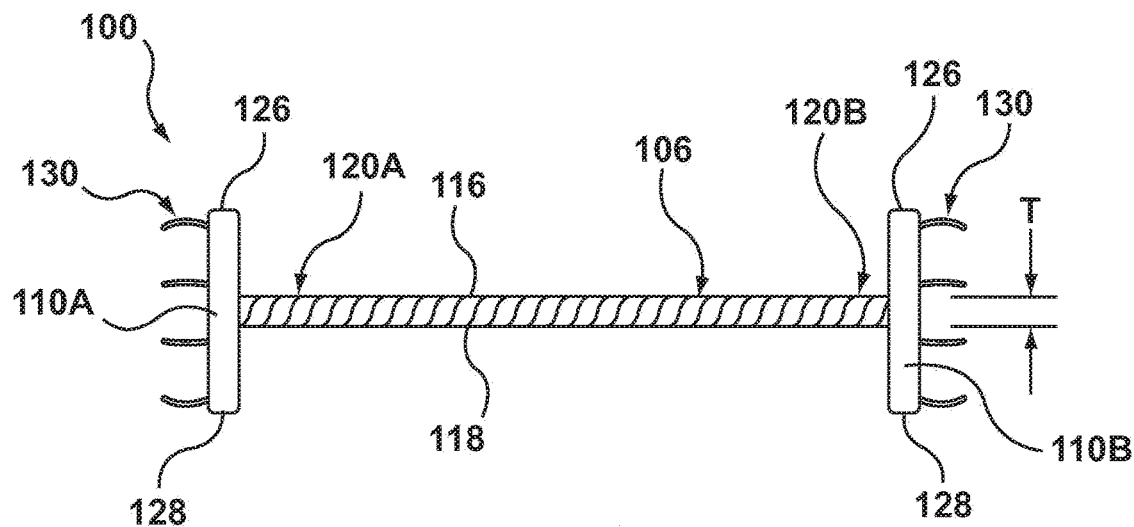
FIG. 2 is a side view of the valve prosthesis of FIG. 1 in an expanded configuration.
Figure 3:
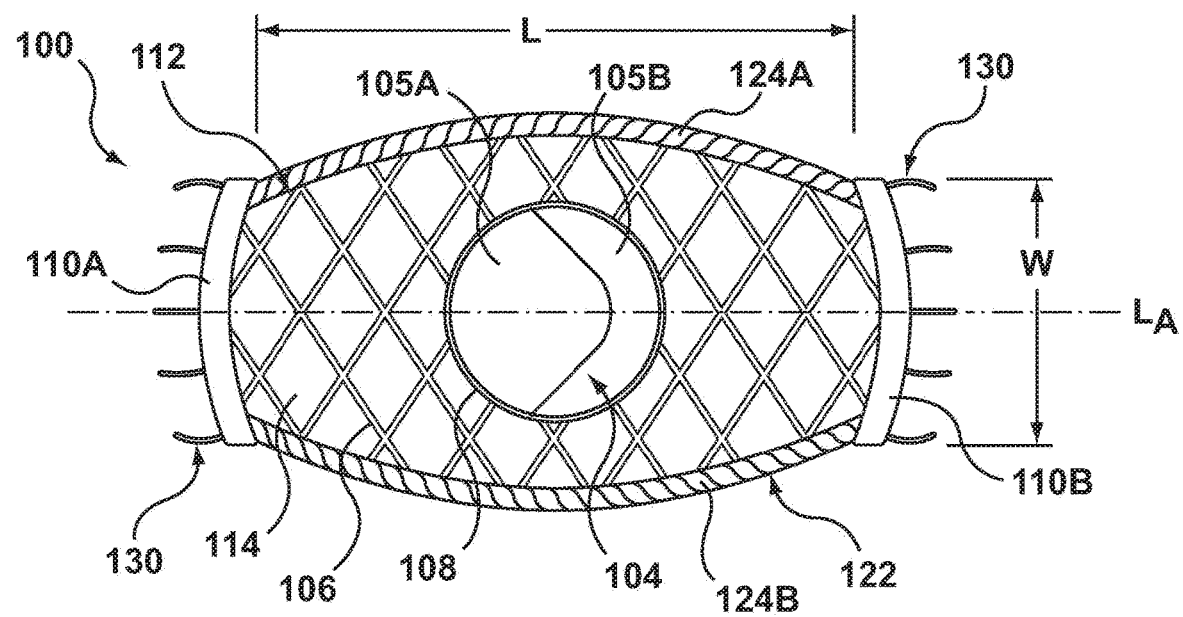
FIG. 3 is a side view of the valve prosthesis of FIG. 1 in an expanded configuration.

More particularly, valve receiving portion 106 of frame 102 is a collapsible, compressible structure made of a material having resiliency or shape memory characteristics in order to return valve prosthesis 100 to the expanded, deployed configuration shown in FIGS. 1-3 upon release from a delivery device, such as delivery catheter 440. More particularly, in the expanded, deployed configuration of FIGS. 1-3, valve receiving portion 106 has a mesh or lattice configuration with diamond-shaped openings 114 defined by the framework thereof, the diamond-shaped openings being shown by way of illustration and not limitation. Valve receiving portion 106 is substantially planar. As utilized here, "substantially planar" includes a structure that has a flat profile with a minimal thickness T that provides valve prosthesis 100 with a low ventricular profile that does not interfere with the left ventricular outflow tract. In an embodiment, thickness T may be in the range of 0.025 mm to 5 mm. The substantially planar configuration of valve receiving portion 106 has opposing upstream and downstream surfaces 116, 118 that extend between opposing first and second ends 120A, 120B thereof, as best shown in the side view of FIG. 2. As best shown in the top view of FIG. 3, valve receiving portion 106 has an oblong shape with a longitudinal length L that is greater than a transverse width W that extends around prosthetic valve component 104 with a perimeter or border that defines an apposition surface 112 thereabout. In an embodiment, width W may be in the range of 2.5 cm to 7.5 cm and length L may be in the range of 3 cm to 8 cm. "Oblong" as utilized herein includes a structure that has a rectangular shape or configuration, with angular or rounded corners, as well as an oval or other rounded shape or configuration. Apposition surface 112 about the perimeter of valve receiving portion 106 maintains apposition of valve prosthesis 100 against the native anatomy to provide a seal there against.

One or both longitudinally extending edges or sides of apposition surface 112 of valve receiving portion 106 may be covered with a sealing component 122 to aid in providing a seal against the native anatomy when valve prosthesis 100 is deployed within the heart. In an embodiment, sealing component 122 includes a first segment 124A of sealing or graft material coupled to one longitudinally extending edge of apposition surface 112 and a second segment 124E of sealing or graft material coupled to the opposing longitudinally extending edge of apposition surface 112. The sealing or graft material of sealing component 122 may be a low-porosity woven fabric, such as polyester, DACRON® fabric, or PTFE. In an embodiment, the sealing or graft material may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the sealing or graft material of sealing component 122 may also be of a natural material such as pericardium or another membranous tissue such as intestinal submucosa or may be a polymer or compressible foam. Notably, sealing component 122 is omitted from the side view of FIG. 2 in order to more clearly illustrate the substantially planar configuration of valve receiving portion 106; however, segments 124A, 124B of sealing material are attached to the longitudinal edges of valve receiving portion 106 and extend between anchors 110A, 110B.

Prosthetic valve component 104 is secured within valve receiving portion 106 and is configured as a one-way valve to allow blood flow in one direction and thereby regulate blood flow there through. In an embodiment, prosthetic valve component 104 includes two valve leaflets 105A. 105B to form a bicuspid replacement valve that closes with pressure on the outflow and opens with pressure on the inflow. In other embodiments in accordance herewith, the prosthetic valve component may be a tricuspid replacement valve or may be a single leaflet replacement valve. The valve leaflets are sutured or otherwise securely and sealingly attached to an inner circumference of valve receiving portion 106 to span across central opening 108 thereof. In an embodiment, central opening 108 is circular although the shape is shown by way of illustration and not limitation. Natural tissue for forming prosthetic valve leaflets for use in prosthetic valve component 104 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals, such as tissue from bovine, equine or porcine origins. Synthetic materials suitable for use as prosthetic valve leaflets in embodiments hereof include DACRON® polyester commercially available from Invista North America S.A.R.L. of Wilmington, Del., polyurethane, Gore-Tex or other cloth materials, nylon blends, polymeric materials, and vacuum deposition nitinol fabricated materials. One polymeric material from which the replacement valve leaflets can be made is an ultra-high molecular weight polyethylene material commercially available under the trade designation DYNEEMA from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Self-expanding frame 102 also includes first and second anchors 110A, 110B, which are disposed at opposing first and second ends 120A, 120B of valve receiving portion 106. First and second anchors 110A, 110B may also be referred to herein as distal and proximal anchors 110A, 110B, respectively. Anchors 110A, 1108 operate to fix or secure valve prosthesis 100 within the native anatomy, and also operate to pin or push back the native leaflets so that the native leaflets do not interfere with operation of valve prosthesis 100. Each anchor 110A, 110B is a thin plate that has a substantially planar or flat body prior to implantation. In the expanded, deployed configuration of FIGS. 1-3, each anchor curves or rounds with its respective end 120A, 120B and is oriented substantially perpendicular to valve receiving portion 106. More particularly, each anchor 110A, 110E may be rectangular, square, oval, rounded, or have another shape or configuration with opposing first and second edges 126, 128. When in the expanded, deployed configuration and oriented substantially perpendicular to valve receiving portion 106, first edge 126 of each anchor 110A, 110B extends outwardly beyond or upstream relative to upstream surface 116 of valve receiving portion 106 and second edge 128 of each anchor 110A, 110B extends outwardly beyond or downstream relative to downstream surface 118 of valve receiving portion 106. "Substantially perpendicular" as utilized herein includes anchors which form an angle between 80 and 100 degrees with respect to the valve receiving portion 106 of the valve prosthesis, prior to implantation thereof. Although initially formed with a flat or planar body, each anchor 110A, 100B is formed from a flexible material that conforms to native anatomy in situ and maintains apposition of valve prosthesis 100 against the native anatomy to provide a seal there against. For example, anchors 110A, 110B may be formed from a material having resiliency or shape memory characteristics in order to return valve prosthesis 100 to the expanded, deployed configuration shown in FIG. 1-3 upon release from a delivery device, such as delivery catheter 440. Accordingly, after implantation of valve prosthesis 100, the body of each anchor 110A, 110B may no longer be flat or planar but may rather be curved or otherwise shaped to conform to the native anatomy. In an embodiment hereof, in order to supplement the radial force provided by the resilient or shape memory material, an adhesive (not shown) may be applied to an outermost surface of each anchor 110A, 110B to aid in securing the anchors to the surrounding native anatomy and maintaining apposition of valve prosthesis 100 against the native anatomy. Such an adhesive layer also aids acts as a sealant and aids in preventing paravalvular leakage in situ. In an embodiment, valve receiving portion 106 and anchors 110A, 110B may be initially formed separately and then joined together by any means known to one of ordinary skill in the art such as, for instance, welding, gluing or suturing. In another embodiment, valve receiving portion 106 and anchors 110A, 110B may be initially formed as a single, integral component.

A plurality of barbs or pins 130 may be coupled to each of first and second anchors 110A, 110B in order to assist in securing valve prosthesis 100 within the native valve annulus after implantation. Barbs 130 extend outwardly away from frame 102 and embed or press into the native anatomy. Barbs 130 may be coupled adjacent to the edges or perimeter of anchors 110A, 110B, as shown in FIG. 1, or may be coupled to anchors 110A, 110B in any other suitable pattern or spacing.

FIGS. 4 and 5 depict valve prosthesis 100 in its compressed, delivery configuration within delivery catheter 440. In an embodiment, first and second anchors 110A, 110E are disposed or flattened under valve receiving portion 106 such that the entire valve prosthesis 100 is substantially planar or flattened. As best shown in FIG. 5, substantially flattened valve prosthesis 100 is then rolled or curled along its longitudinal axis $L_A$ (shown in FIG. 3) in order to compress or collapse valve prosthesis 100 into a smaller diameter suitable for transcatheter delivery. It will be understood by one of ordinary skill in the art that the compressed, delivery configuration of valve prosthesis 100 is not limited to the rolled or curled configuration shown in FIGS. 4-5 but rather is only an exemplary method utilized to compress or collapse valve prosthesis 100 into a suitable profile for transcatheter delivery.

Delivery catheter 440 includes an outer sheath 442 and an inner tube 444 slidingly disposed therein such that outer sheath 442 and inner tube 444 are moveable relative to each other. Although only a distal portion of delivery catheter 440 is shown, it will be understood by those of ordinary skill in the art that both outer sheath 442 and inner tube 444 extend to the proximal end of delivery catheter 440 to be assessable by the clinician. Valve prosthesis 100 in its compressed, delivery configuration is disposed within a distal portion of outer sheath 442, distal to a distal end 446 of inner tube 444, such that outer sheath 442 maintains the valve prosthesis in its compressed configuration during delivery. Valve prosthesis 100 abuts against and contacts distal end 446 of inner tube 444. Although not required, inner tube 444 may define a lumen therethrough (not shown) for accommodating a guidewire.

When it is desired to deploy valve prosthesis 100 in situ, outer sheath 442 is proximally retracted to expose first anchor 110A and a portion of valve receiving portion 106 that is adjacent to first anchor 110A. Second anchor 110B and the remainder of valve receiving portion 106 remains compressed within outer sheath 442. Once released from delivery catheter 440, first anchor 110A and a portion of valve receiving portion 106 adjacent thereto unrolls or uncurls and self-expands to the expanded, deployed configuration of FIGS. 1-3. More particularly, when first anchor 110A self-expands to the expanded, deployed configuration, the thin plate that forms first anchor 110A first unrolls or uncurls to resume a flattened or planar configuration. First anchor 110A, which is now flattened but still disposed under valve receiving portion 106, then resumes its expanded, deployed configuration in which it extends substantially perpendicular to the valve receiving portion by flipping outwardly or rotating about end 120A of valve receiving portion 106. In an embodiment in which valve prosthesis 100 is deployed to replace a native mitral valve, first anchor 110A engages and pins back the native anterior leaflet of the native mitral valve as will be explained in more detail below. Outer sheath 442 is then further proximally retracted to expose second anchor 110E and the remainder of valve receiving portion 106 such that they may unroll or uncurl and return or self-expand to the expanded, deployed configuration shown in FIGS. 1-3. Second anchor 110B self-expands to the expanded, deployed configuration in the same manner as described above with respect to anchor 110A. The thin plate that forms second anchor 110B first unrolls or uncurls to resume a flattened or planar configuration, and then flips outwardly or rotates about end 120B of valve receiving portion 106 in order to resume its expanded, deployed configuration in which it extends substantially perpendicular to the valve receiving portion. In an embodiment in which valve prosthesis 100 is deployed to replace a native mitral valve, valve receiving portion 106 is deployed to seat within the annulus of the native mitral valve and second anchor 110B engages and pins back the native posterior leaflet of the native mitral valve as will be explained in more detail below. During retraction of outer sheath 442 to deploy valve prosthesis 100, inner tube 444 operates or functions as a retainer or stop that prevents valve prosthesis 100 from proximally retracting in conjunction with outer sheath 442. In another embodiment hereof, inner tube 444 may operate or function as a pusher tube which is distally advanced relative to outer sheath 442 to deploy valve prosthesis 100 as will be understood by one of ordinary skill in the art.

Figure 7:
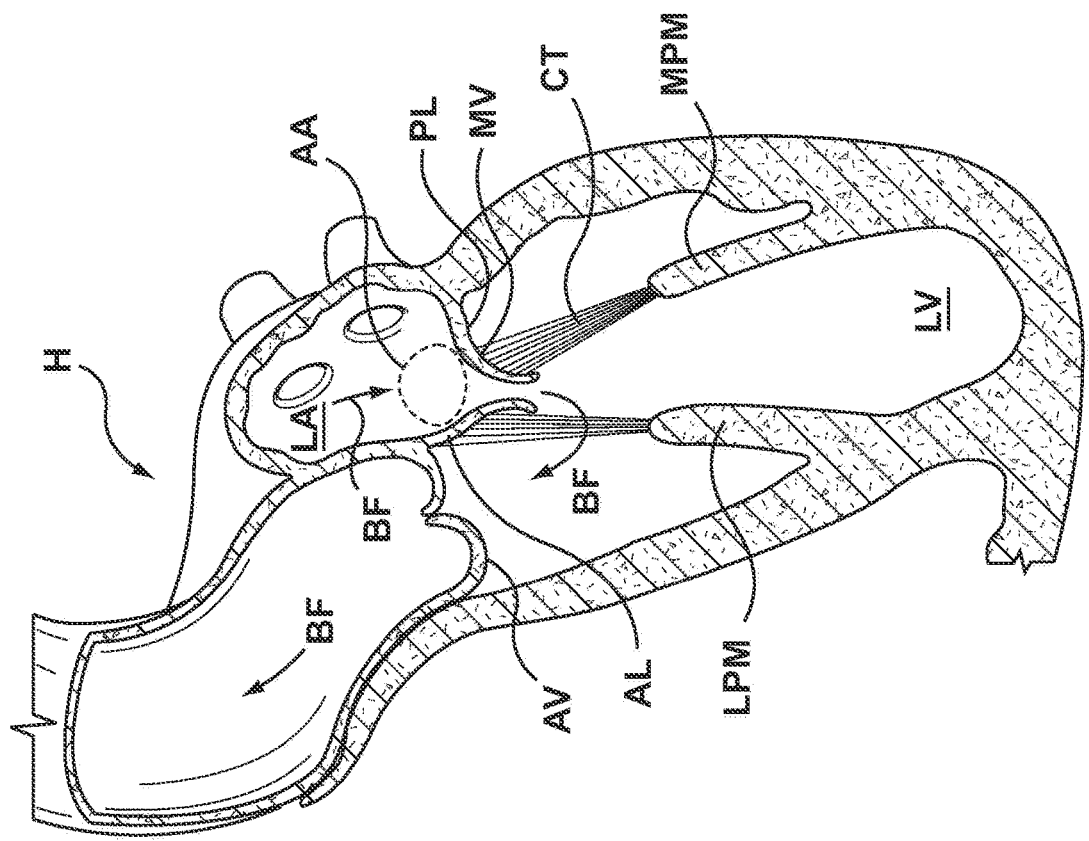
FIG. 7 also illustrates an access zone for performing transcatheter valve replacement of the mitral valve in accordance with an embodiment hereof.

FIGS. 6-10 illustrate a method of delivering and implanting valve prosthesis 100 in accordance with an embodiment hereof to perform a heart valve replacement procedure, more particularly a mitral valve replacement, with minimal blood flow stoppage or interruption. With reference to FIG. 7, illustrating a cross-sectional view of a heart H, the heart H includes a left atrium LA, a left ventricle LV, a mitral valve MV and an aortic valve AV, Blood flow BF is depicted with directional arrows in FIG. 7 in the left atrium LA, into left ventricle LV through mitral valve MV, and into the aorta through aortic valve AV. Mitral valve MV is saddle-shaped and includes two native leaflets, posterior leaflet PL and anterior leaflet AL, and chordae tendineae CT extend within the left ventricle LV between the native leaflets of the mitral valve MV and the papillary muscles. More particularly, chordae tendineae CT are cord-like tendons that connect, the medial papillary muscle MPM to the posterior leaflet PL of the mitral valve MV and connect the lateral papillary muscle LPM to the anterior leaflet AL of the mitral valve MV. When the native mitral valve is operating properly, the native leaflets will generally function in such a way that blood flows toward the left ventricle LV when the leaflets are in an open position, and so that blood is prevented from moving toward the left atrium LA when the leaflets are in a closed position. During systole, when the native leaflets close to prevent backflow of blood into the atrium, the chordae tendineae CT assist in preventing the native leaflets from everting or prolapsing into the atrium by becoming tense and holding the native leaflets in the closed position. In accordance with an embodiment hereof, a valve prosthesis 100 can be positioned in the area of a malfunctioning mitral valve MV in accordance with the invention, thereby replacing the mitral valve. Advantageously, the method of use described herein utilizes side access into the heart H and the deployed, expanded configuration of anchors 110A, 110E of valve prosthesis 100 to move or push the native leaflets of the mitral valve MV out of the mitral valve space so that they do not interfere with operation of the valve prosthesis. In addition, side access into the left atrium LA of the heart H and the substantially planar deployed, expanded configuration of valve receiving portion 106 of valve prosthesis 100 avoids or minimizes interference with the chordae tendineae CT present in the left ventricle LV of the heart H.

Figure 6:
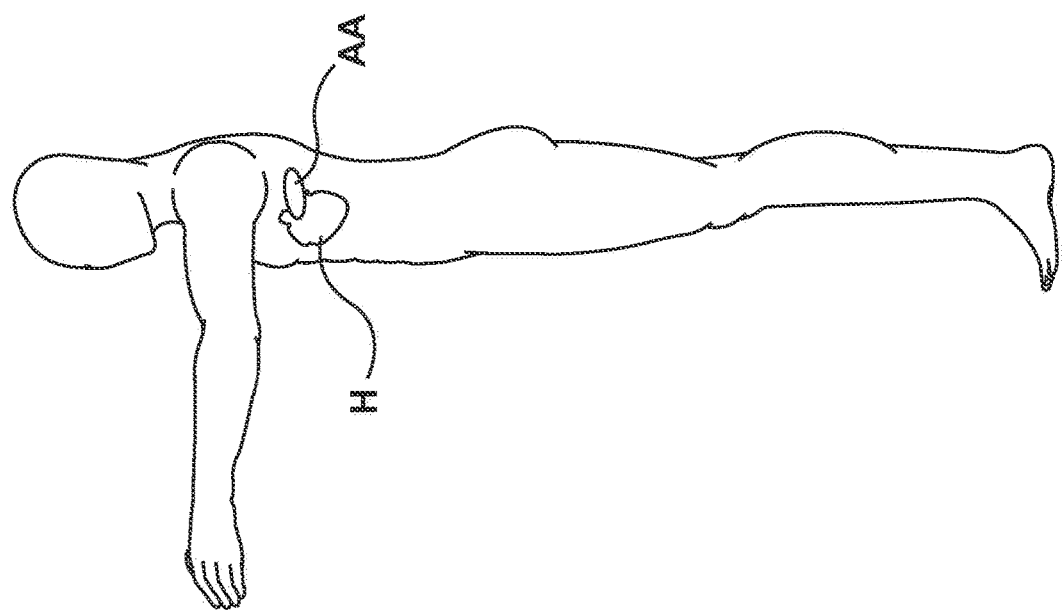
FIG. 6 illustrates an access zone for performing transcatheter valve replacement of the mitral valve in accordance with an embodiment hereof.

FIGS. 6 and 7 illustrate an access zone or area AA for a left thoracotomy approach for a transcatheter or minimally invasive mitral valve replacement procedure. The left-sided approach offers some unique advantages, including a relatively shorter distance to the mitral valve over a right-sided approach as well as access within the mitral valve that allows the native valve leaflets to be moved or repositioned as will be described in more detail herein. Initially, a relatively short incision, approximately 5-8 cm in length, may be made in the fourth, fifth, or sixth intercostal space. In an embodiment hereof, deflation of the left lung may be performed prior to and/or concurrent with introduction of delivery catheter 440, and the deflated left lung may be repositioned to expose the heart. An incision or opening may be formed in the pericardium, anteriorly or posteriorly to the phrenic nerve depending on the individual anatomy, and another incision or opening may be formed in a wall of the left atrium LA, slightly superior to an annulus of the native mitral valve MV, to provide exposure of the native mitral valve MV. Delivery catheter 440 having valve prosthesis 100 in a delivery configuration therein (not shown in FIG. 7) is advanced to the heart and through the incision of the left atrium LA until at least a distal portion of the delivery catheter, i.e., the distal portion containing valve prosthesis 100 contained therein, is disposed within or adjacent to the native mitral valve MV. In an embodiment, delivery catheter 440 so positioned may have been tracked through a trocar or other introducer device (not shown) that has been inserted through purse-string sutures (not shown) previously placed in the left atrium LA. The purse-string sutures would be tightened around the trocar or other introducer device and a hemostasis valve would also be used to minimize blood leakage from the heart during the percutaneous replacement-valve implantation procedure, as would be understood by one of ordinary skill in the art. As previously noted, the proximal ends (not shown) of delivery catheter 440 and its components extend out of the body to be accessible by a clinician.

Figure 8:
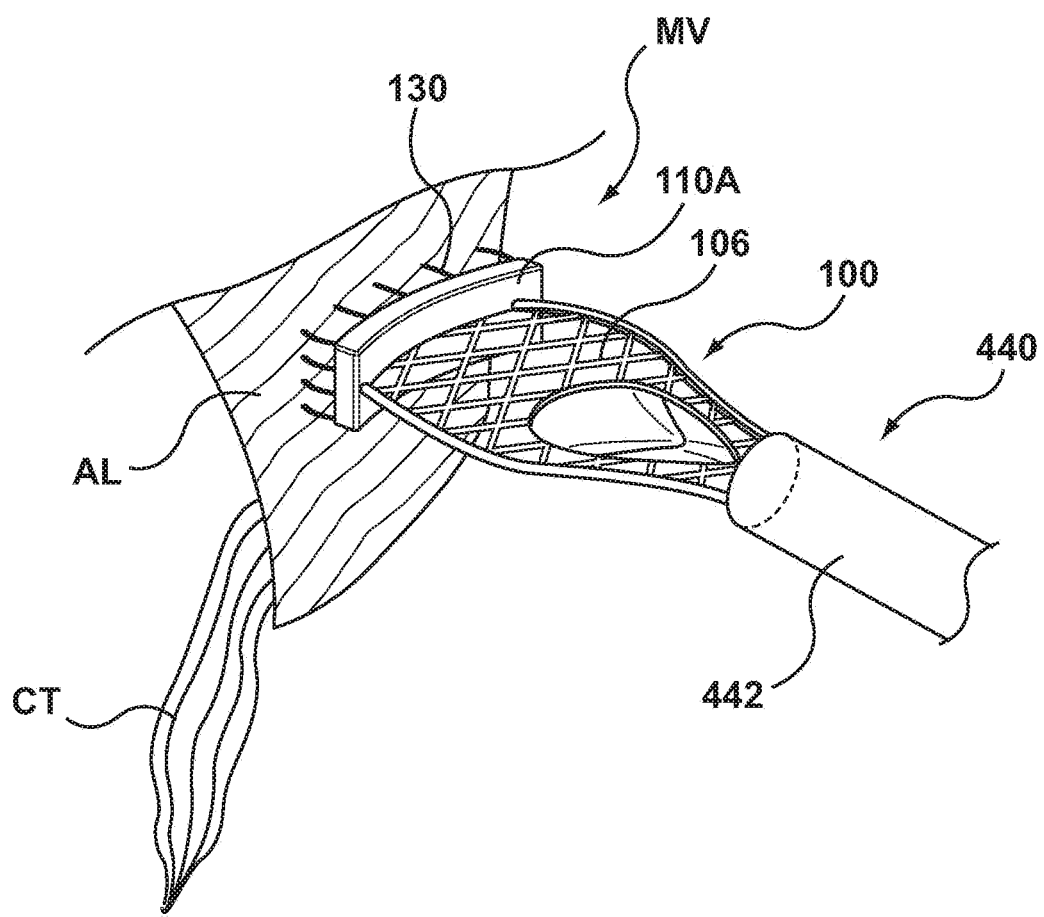
FIG. 8 illustrates a step of a method of performing a transcatheter valve replacement of the mitral valve in accordance with an embodiment hereof.

Once the distal portion of delivery catheter 440 is positioned proximate to the native mitral valve MV as desired, first or distal anchor 110A of valve prosthesis 100 is released by retracting outer sheath 442 of delivery system 440 by a sufficient amount that this portion of the prosthesis is exposed as shown in FIG. 8. Due to the self-expanding properties thereof, distal anchor 110A and a portion of valve receiving portion 106 adjacent thereto will expand radially outwardly relative to the sheath in which it was enclosed and return to the expanded, deployed configuration in which distal anchor 110A is oriented substantially perpendicular to valve receiving portion 106. During deployment of distal anchor 110A, second or proximal anchor 110B and the remainder of valve receiving portion 106 remain in the compressed configuration within outer sheath 442 of delivery catheter 440.

Figure 9:
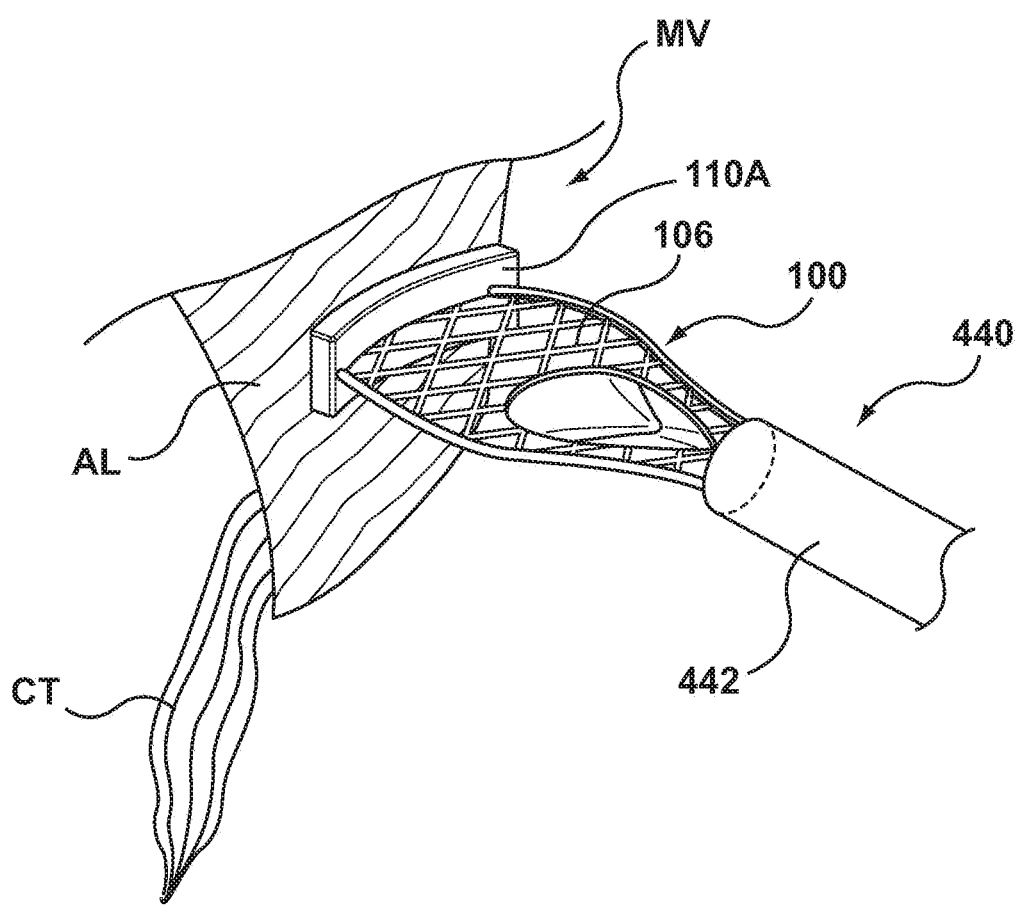
FIG. 9 illustrates a step of a method of performing a transcatheter valve replacement of the mitral valve in accordance with an embodiment hereof.

Distal anchor 110A of valve prosthesis 100 is then secured to a wall of the heart as shown in FIG. 9. More particularly, valve prosthesis 100 is distally advanced through distal advancement of inner tube 444 (not visible in the view of FIG. 9) until distal anchor 110A contacts or abuts against the wall of the heart. The anterior leaflet AL of the native mitral valve MV is pinned or captured between the wall of the heart and distal anchor 110A. When pressed against the wall of the heart, distal anchor 110A conforms to the wall of the heart and barbs 130 (visible in FIG. 8 but not visible in the view of FIG. 9) are pressed into the wall of the heart to assist in securing the prosthesis to the native anatomy. Alternatively, distal anchor 110A may contact the wall of the heart and be secured thereto upon release from delivery catheter 440 and self-expansion thereof without requiring additional positioning thereof.

Figure 10:
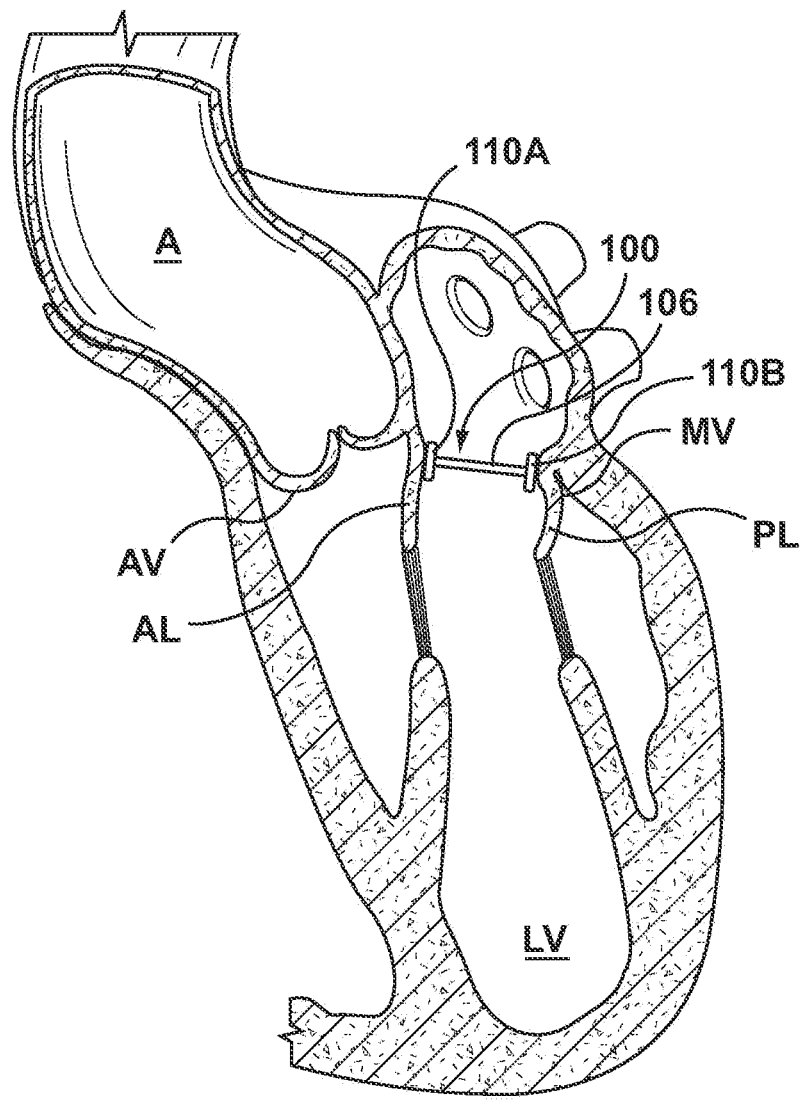
FIG. 10 illustrates a step of a method of performing a transcatheter valve replacement of the mitral valve in accordance with an embodiment hereof..

Continued proximal retraction of outer sheath 442 releases the remainder of valve prosthesis 100, including second or proximal anchor 110B, from delivery catheter 440. Due to the self-expanding properties thereof, proximal anchor 110B and the remainder of valve receiving portion 106 expands radially outwardly relative to the sheath in which it was enclosed and return to the expanded, deployed configuration in which the proximal anchor is oriented substantially perpendicular to valve receiving portion 106 as shown in FIG. 10 (delivery catheter 440 is omitted from the view of FIG. 10 for sake of clarity). Upon release from delivery catheter 440, proximal anchor 110B contacts the wall of the heart and is secured thereto, thereby pinning or capturing the posterior leaflet PL of the native mitral valve MV between the wall of the heart and proximal anchor 110B. When pressed against the wall of the heart, proximal anchor 110E conforms to the wall of the heart and barbs 130 are pressed into the wall of the heart to assist in securing the prosthesis to the native anatomy. All frame components, i.e., valve receiving portion 106 and anchors 110A, 1108, deploy or expand within the heart to be in apposition with the native mitral valve and functions as a replacement mitral valve. More particularly, the frame components exert an apposition force that acts against the annulus of the native mitral valve and/or any heart structure in which they come in contact to seal against paravalvular leakage. After implantation of valve prosthesis 100, delivery catheter 440 is removed from the heart with the purse-string sutures noted above being tightened thereafter to close the opening in the left atrium.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of percutaneously delivering and deploying a valve prosthesis within a native valve of a heart comprising:

introducing a portion of a delivery system into a patient, the delivery system including a delivery catheter and the valve prosthesis in a compressed delivery configuration in a distal portion of the delivery catheter, wherein the valve prosthesis includes a self-expanding frame and a prosthetic valve component, the self-expanding frame having a first end, a second end opposing the first end, an upstream surface, and a downstream surface opposing the upstream surface and being configured to be positioned downstream of the upstream surface in situ, wherein the upstream surface and the downstream surface each extend between the first end and the second end of the self-expanding frame, and wherein the valve prosthesis in the compressed delivery configuration is disposed within the delivery catheter such that the first end of the self-expanding frame is distal to the second end of the self-expanding frame;

advancing the valve prosthesis until at least a portion of the valve prosthesis is disposed within the native valve;

retracting an outer sheath of the delivery system to deploy the first end of the self-expanding frame, wherein at least the second end of the self-expanding frame remains in the distal portion of the delivery catheter;

securing the first end of the self-expanding frame to a wall of the heart, wherein a first native leaflet of the native valve is thereby pinned between the wall of the heart and the first end;

retracting the outer sheath of the delivery system to deploy the second end of the self-expanding frame such that the valve prosthesis is in an expanded configuration; and securing the second end of the self-expanding frame to the wall of the heart, wherein a second native leaflet of the native valve is thereby pinned between the wall of the heart and the second end.

2. The method of claim 1, wherein a longitudinal axis of the valve prosthesis extends between the first end and the second end of the self-expanding frame and wherein the valve prosthesis in the compressed delivery configuration is disposed within the delivery catheter such that the longitudinal axis of the valve prosthesis is parallel to a longitudinal axis of the delivery catheter.

3. The method of claim 2, wherein the valve prosthesis in the compressed delivery configuration is rolled along its longitudinal axis in order to compress the valve prosthesis into the delivery catheter.

4. The method of claim 1, wherein during the step of introducing the delivery system, the delivery system is advanced through the wall of an atrium superior to an annulus of a native mitral valve.

5. The method of claim 1, wherein at least a portion of the prosthetic valve component remains in the distal portion of the delivery catheter during the step of retracting the outer sheath of the delivery system to deploy the first end of the self-expanding frame.

6. The method of claim 1, wherein the step of securing the second end of the self-expanding frame to the wall of the heart occurs via self-expansion of the self-expanding frame.

7. The method of claim 1, wherein the valve prosthesis further includes a sealing component coupled to the self-expanding frame, the sealing component includes a first segment of sealing material secured to a first longitudinally-extending edge of the self-expanding frame and a second segment of sealing material secured to an opposing second longitudinally-extending edge of the self-expanding frame.

8. The method of claim 1, wherein the self-expanding frame has a valve receiving portion that defines a central opening and the prosthetic valve component including at least two leaflets sealingly and directly attached to the valve receiving portion to span across the central opening thereof, and wherein the prosthetic valve component and the valve receiving portion collectively have a flat profile in situ after the step of securing the second end of the self-expanding frame to the wall of the heart.

9. The method of claim 1, wherein the native valve is a mitral valve.

10. The method of claim 9, wherein the first native leaflet is an anterior leaflet of a native mitral valve and the second native leaflet is a posterior leaflet of a native mitral valve.

11. The method of claim 1, wherein the step of introducing a portion of a delivery system into a patient includes introducing the portion of the delivery system into the heart of the patient through a left sided thoracotomy.

12. The method of claim 1, wherein the self-expanding frame has a valve receiving portion that defines a central opening and the prosthetic valve component including at least two leaflets sealingly and directly attached to the valve receiving portion to span across the central opening thereof, and wherein a first anchor is disposed at the first end of the self-expanding frame and a second anchor is disposed at the second end of the self-expanding frame.

13. The method of claim 12, wherein each of the first anchor and the second anchor is oriented substantially perpendicular to the valve receiving portion when the valve prosthesis is in the expanded configuration.

14. The method of claim 13, wherein each of the first anchor and the second anchor is a plate having a substantially flat body formed from a flexible material that conforms to native anatomy in situ and wherein each of the proximal anchor and the distal anchor conforms to the wall of the heart during the respective steps of securing the first end and the second end of the self-expanding frame to the wall of the heart.

15. The method of claim 13, wherein the valve prosthesis further includes a plurality of barbs coupled to each of the first anchor and the second anchor, the barbs extending outwardly away from the self-expanding frame, and the steps of securing the first end and the second end of the self-expanding frame to the wall of the heart includes pressing the barbs into the wall of the heart.

16. The method of claim 13, wherein a longitudinal axis of the valve prosthesis extends between the first end and the second end of the self-expanding frame and wherein each of the first anchor and the second anchor is disposed under the valve receiving portion of the self-expanding frame and the valve prosthesis is rolled along its longitudinal axis when the valve prosthesis is in the compressed delivery configuration.

17. The method of claim 1, wherein the self-expanding frame has a valve receiving portion that defines a central opening and the prosthetic valve component including at least two leaflets sealingly and directly attached to the valve receiving portion to span across the central opening thereof, and wherein the valve receiving portion includes a mesh that defines a plurality of openings and the central opening, the mesh extending between the first and second ends of the self-expanding frame such that the central opening and the plurality of openings are oriented transverse to blood flow in situ after the step of securing the second end of the self-expanding frame to the wall of the heart.

18. The method of claim 1, wherein a longitudinal axis of the valve prosthesis extends between the first end and the second end of the self-expanding frame and wherein the self-expanding frame has a longitudinal length along its longitudinal axis that is greater than a transverse width perpendicular to its longitudinal axis.

19. The method of claim 1, wherein a longitudinal axis of the valve prosthesis extends perpendicular to blood flow in situ through the prosthetic valve component of the valve prosthesis when the valve prosthesis is in the expanded configuration.

20. A method of percutaneously delivering and deploying a valve prosthesis within a native valve of a heart comprising:

introducing a portion of a delivery system into a patient, the delivery system including a delivery catheter and the valve prosthesis in a compressed delivery configuration in a distal portion of the delivery catheter, wherein the valve prosthesis includes a self-expanding frame and a prosthetic valve component, and wherein a longitudinal axis of the valve prosthesis extends between a first end of the self-expanding frame and a second end of the self-expanding frame, the longitudinal axis of the valve prosthesis being configured to extend perpendicular to blood flow in situ through the prosthetic valve component of the valve prosthesis when the valve prosthesis is in an expanded configuration, and wherein the valve prosthesis in the compressed delivery configuration is disposed within the delivery catheter such that the longitudinal axis of the valve prosthesis is parallel to a longitudinal axis of the delivery catheter;

advancing the valve prosthesis until at least a portion of the valve prosthesis is disposed within the native valve;

retracting an outer sheath of the delivery system to deploy the first end of the self-expanding frame, wherein at least the second end of the self-expanding frame remains in the distal portion of the delivery catheter;

securing the first end of the self-expanding frame to a wall of the heart, wherein a first native leaflet of the native valve is thereby pinned between the wall of the heart and the first end;

retracting the outer sheath of the delivery system to deploy the second end of the self-expanding frame such that the valve prosthesis is in the expanded configuration; and securing the second end of the self-expanding frame to the wall of the heart, wherein a second native leaflet of the native valve is thereby pinned between the wall of the heart and the second end.

\* \* \* \* \*